United States Patent
Curiel et al.

(12)
(10) Patent No.: US 6,440,078 B1
(45) Date of Patent: Aug. 27, 2002

(54) METHOD AND SYSTEM OF DETERMINING CARDIAC CONTRACTILITY

(76) Inventors: Roberto Curiel, Calle Caurimare, Residencias Iviipa, Apto. 3B, Colinas de Bello Monte; Ruben Landecta, Avda, Sucre, Residencia Yutaje, Torre B, Apto. 242, Los dos Carminos, both of Caracas; Mauro Herrera, Residencias Las Trinitarias, Torre D, Apto 63D, Avda, Jose M, Vargas, Sta. Fe Norte; Miguel Cerrolaza, Calle Caurimare, Residencia Mirasierra, Apto. 14B, Colinas de Bello Monte, Caracas, all of (VE)

( * ) Notice: Subject to any disclaimer, the term of this patent is extended or adjusted under 35 U.S.C. 154(b) by 14 days.

(21) Appl. No.: 09/621,774

(22) Filed: Jul. 21, 2000

Related U.S. Application Data

(60) Provisional application No. 60/145,436, filed on Jul. 23, 1999.

(51) Int. Cl.$^7$ .................................................. A61B 5/02
(52) U.S. Cl. ...................................... 600/481; 600/508
(58) Field of Search ................................ 600/481, 485, 600/508

(56) References Cited

U.S. PATENT DOCUMENTS

| | | | |
|---|---|---|---|
| 4,677,984 A | | 7/1987 | Sramek |
| 5,103,828 A | * | 4/1992 | Sramek ................ 600/481 |
| 5,139,020 A | | 8/1992 | Koestner et al. |
| 5,390,679 A | | 2/1995 | Martin |
| 5,400,793 A | | 3/1995 | Wesseling |
| 5,535,753 A | | 7/1996 | Petrucelli et al. |
| 5,584,298 A | | 12/1996 | Kabal |
| 5,647,369 A | | 7/1997 | Petrucelli et al. |
| 5,758,652 A | | 6/1998 | Nikolic |
| 5,836,884 A | | 11/1998 | Chio |
| 5,913,826 A | | 6/1999 | Blank |
| 6,077,236 A | | 6/2000 | Cunningham |
| 6,090,047 A | * | 7/2000 | Kass et al. .................. 600/485 |

OTHER PUBLICATIONS

Hoka, S. "Relationship among the heart, vasculature and blood volume at perioperative period: the influence of volatile anesthetics." Masui. 1996 Jun; 45(6): 707–16.*
Rogers, James. "Cardiovascular Physiology." Update in Anaesthesia. 1999; Issue 10, Article 2: 2–8.*

* cited by examiner

*Primary Examiner*—Robert L. Nasser
*Assistant Examiner*—Patricia Mallari
(74) *Attorney, Agent, or Firm*—Sampson & Associates

(57) ABSTRACT

Provided are methods of determining the cardiac contractility of a cardiovascular system, which methods comprise a step of utilizing values representing stroke volume, preload, and afterload to calculate the cardiac contractility. Most preferably, the calculation of cardiac contractility utilizes a mathematical relationship where the stroke volume is represented by the volume of a tetrahedron, the preload is represented by a length of the base of the base triangle of the tetrahedron, the afterload is represented by the height of the base triangle of the tetrahedron, and the cardiac contractility is represented by the height of the tetrahedron. Also provided are measurement systems for determining the cardiac contractility of a cardiovascular system that utilize such methods of determining cardiac contractility.

19 Claims, No Drawings

METHOD AND SYSTEM OF DETERMINING CARDIAC CONTRACTILITY

This application claims the benefit of provisional application 60/145,436 filed on Jul. 23, 1999.

FIELD OF THE INVENTION

The present invention relates in general to cardiovascular measurement and more particularly to methods and systems for determining cardiac contractility.

BACKGROUND OF THE INVENTION

Throughout this application, various publications and patents are referred to by an identifying citation. The disclosures of the publications and patents referenced in this application are hereby incorporated by reference into the present disclosure to more fully describe the state of the art to which this invention pertains.

Almost any cardiac disorder that impairs the ability of the ventricle to eject blood suffers a progression toward an inexorable deterioration of cardiac structure and function, producing the complex clinical syndrome of heart failure, which is a common medical condition that afflicts approximately 1.5 to 2.0% of the population (4.8 million people in the United States) and which has a risk of death of 5 to 10% annually in patients with mild symptoms and increases to as high as 30 to 40% annually in patients with advanced disease, as, for example, described in 1998 *Heart and Stroke Statistical Update* by the American Heart Association, Dallas, Tex., 1997; *Am. Heart J.*, Vol. 133, pages 703 to 712 (1997) by Massie et al.;*J. Heart Lung Transplant*, Vol. 13, pages S107 to S112 (1994) by O'Connell et al.; and *Am. Coll. Cardiol.*, Vol. 22 (Suppl. A.), pages 6A to 13A (1993) by Ho et al. Annual direct expenditures for heart failure in the United States have been estimated at $20 to 40 billion, twice that for all forms of cancer, as described in the above-mentioned references by Massie et al. and O'Connell et al.

The core of the altered cardiac function in heart failure is a depression of cardiac contractility, as, for example, described in *Lancet*, Vol. 352 (Suppl. I), pages 8 to 14 (1998) by Bristow. Therefore, an adequate assessment of cardiac contractility has important diagnostic and therapeutic implications. Patients with acute heart failure, particularly as a complication of acute myocardial infarction or as an acute exacerbation of a previously compensated chronic heart failure, have a high mortality rate of about 30% within the first 12 months. In this clinical condition, a proper evaluation of cardiac contractility is extremely important for diagnostic purposes to assess the severity of the process and as a guide for the inotropic therapy. Typically, ejecting phase indices are used to evaluate ventricular function with the serious limitations that these parameters have, especially in this clinical setting where frequent and prominent hemodynamic load changes occur, as, for example, described in *Arch. Mal. Coeur. Vaiss.*, Vol. 91, pages 1349 to 1358 (1998) by Bosio et al.; *Rev. Prat.*, Vol. 47, pages 2146 to 2152 (1997) by Garot et al.; and *Fortschr. Med.*, Vol. 115, pages 30 to 34 (1997) by Schwinger et al.

In regards to chronic heart failure, perhaps as many as 20 million individuals in the United States have an asymptomatic impairment of cardiac function and are likely to develop symptoms in the next 1 to 5 years. At this stage of heart failure, a reliable index of cardiac contractility is required for an early identification and appropriate treatment to achieve the greatest impact on individual and public health, as, for example, described in *Am. J. Cardiol.*, Vol. 83, pages 1A to 38A (1999) by Parker et al.

In more advanced stages of heart failure, ventricular function parameters are measured to identify the severity of the cardiac abnormality. In this setting, ejection fraction is widely used. However, it has no good correlation with the physical capacity of the patient, as, for example, described in *Circulation*, Vol. 87 (Suppl. VI), pages VI-88 to VI-93 (1993) by Smith et al.; and *Am. J. Cardiol.*, Vol. 47, pages 33 to 39 (1981) by Franciosa et al. There is debate about the value of repeated measurement of ejection fraction to evaluate the course, prognosis or therapeutic response, as, for example, described in the above-mentioned reference by Parker et al. It is expected that a more refined assessment of cardiac contractility, together with a better knowledge of the peripheral circulation and the neuro-endocrine axes, will improve the evaluation and treatment of these patients.

In severe valve diseases with striking modifications in cardiac loads, adequate information in relation to cardiac contractility, but different to the typically used ejection phase indices, is most important to choose the proper time for surgical treatment, as, for example, described in *Heart Disease*, Braunwald (ed.), W. B. Saunders Company, Philadelphia, 1977, pages 1007 to 1076, by Braunwald.

Contractility or inotropic state of the heart refers to a fundamental property of cardiac tissue and represents the intensity of the active state of the muscle. The level of the inotropic state is given by the interaction of calcium ions and the contractile protein reflecting the level of activation and the formation and cycling of the cross bridges between actin and myosin filaments, as, for example, described in *Heart Disease*, Brunwald (ed.), W. B. Saunders Company, Philadelphia, 1977, pages 421 to 444 by Little et al. This interaction is able to be widely modified by multiple and simultaneous factors such as force-frequency relation, circulating catecholamines, sympathetic nerve impulses, anoxia, hypercapnia, acidosis, pharmacologic intervention, etc., as, for example, described in *J. Cardiovasc. Pharmacol.*, Vol. 26 (Suppl. 1), pages S1 to S9 (1995) by Opie. However, no absolute measure of myocardial contractility exists.

Many indices have been proposed as measures of left ventricular contractile function, analyzing the behavior of changes in pressure and/or volume during the isovolumetric or ejection phase of the left ventricular systole. Some of these indices are shown in Table 1.

TABLE 1

Indices of Cardiac Contractility

I. Isovolumetric Phase Indices
   1. Rate of rise of ventricular pressure (dP/dt):
      a. maximum
      b. dP/dt/P
      c. dP/dt DP40
      d. VPM (dP/dt/28P)
   2. Vmax
II. Ejection Phase Indices
   1. Stroke volume or work/diastolic volume
   2. Ejection fraction (EF)
   3. Velocity of circumferential shortening (Vcf)
   4. Mean normalized systolic ejection rate (MNSER)
   5. FE or Vcf/end-systolic stress Most of these indices of cardiac contractility, such as maximum rate of rise of dP/dt, EF, and Vcf, are highly sensitive to acute inotropic changes, as, for example, described in *From Cardiac Catheterization Data to Hemo-* dynamic Parameters, F. A. Davis Company, Philadelphia, 1988, by Yang et al.; *J. Clin. Invest.*, Vol. 41, page 80 (1962) by Gleason et al.; *Am. J. Cardiol.*, Vol. 31, page 415 (1973) by Krayenbuehl et al.; *Circ. Res.*, Vol. 56, page 808 (1985) by Little; and *Circulation*, Vol. 76, page 1422, by Kass et al. However, these indices are markedly modified by preload or afterload alterations, as described, for example, in the above-mentioned references by Gleason et al., Little, and Kass et al. To overcome these limitations, some modifications of these indices have been proposed, such as for dP/dt/P, dP/dt/DP, VPM, stroke volume, MNSER, and FE or Vcf/ end-systolic stress, which make them less sensitive, though still sensitive, to changes in loads, as, for example, described in *Circulation*, Vol. 44, page 47 (1971) by Mason et al.; *Cardiovasc. Res.*, Vol. 8, page 299 (1974) by Davidson et al.; *Circulation*, Vol. 53, page 293 (1976) by Quinones et al.; *Am. J. Physiol.*, Vol. 240, page H80 (1981) by Carabello et al.; *Ann. Intern. Med.*, Vol. 99, page 750 (1983) by Borow et al.; *J. Am. Coll. Cardiol.*, Vol. 4, page 715 (1984) by Colan et al.; *Circulation*, Vol. 73, page 47 (1986) by Wisenbaugh et al.; *Circulation*, Vol. 78, page 68 (1988) by Mirsky et al.; *Ann. Intern. Med.*, Vol. 108, page 524 (1988) by Lang et al.; and *J. Am. Coll. Cardiol.*, Vol. 20, page 787 (1992) by Borow et al. Even Vmax, which was originally proposed as being independent of load index of cardiac contractility, has theoretical and practical limitations, and it is no longer used for clinical purposes, as, for example, described in *Ann. Rev. Physiol.*, Vol. 34, page 47 (1972) by Ross et al.

Another way to assess cardiac contractility is by analyzing the end-systolic pressure/volume relation (ESPVR or ESP/ESV). The generation of variably afterloaded beats allows determination of several relationships. The slope of this line, usually known as Ees or Emax, denotes the maximum stiffness or elastance of the left ventricle, as, for example, described in *Circ. Res.*, Vol. 35, pages 117 to 126 (1974) by Suga et al.; and *Circulation*, Vol. 69, pages 1058 to 1064 (1984) by Carabello et al. The slope and/or position of the ESPVR respond to changes in myocardial contractile state, as for example, described in *Circulation*, Vol. 69, pages 1058 to 1064 (1984) by Carabello et al.; and *Cardiovasc. Res.*, Vol. 9, pages 447 to 455 (1975) by Mahler et al. This index is independent of preload, and afterload is the controlled variable, as, for example, described in the above-mentioned reference by Suga et al. However, it is not possible to know the resting value of the relationship since alterations in the afterload are required to obtain the slope of the ESPVR. This slope behaves as a straight line for only part of the range of the physiologic values of afterload, as, for example, described in *Am. J. Physiol.*, Vol. 252, pages H1218 to H1227 (1987) by Burkhoff et al.; and *Circulation*, Vol. 79, pages 167 to 178 (1989) by Kass et al. Additionally, no normal value of this slope has been established, and this technique is less sensitive than the isovolumetric and ejection phase indices to assess changes in the inotropic state of the heart, as, for example, described in *Circulation*, Vol. 76, pages 1115 to 1126 (1987) by Crottogini et al.; and *Circulation*, Vol. 76, pages 1422 to 1436 (1987) by Kass et al.

U.S. Pat. No. 5,400,793 to Wesseling describes a method of determining the stroke volume and cardiac output of the human heart from a pulse-type blood-stream pressure signal. U.S. Pat. No. 5,265,165 to Frank et al. describes a method and apparatus for continuous measurement of cardiac output by analyzing the blood pressure signal. U.S. Pat. Nos. 5,535,753 and 5,647,369, both to Petrucelli et al., describe apparatus and methods for non-invasively measuring cardiovascular system parameters involving sensing a time varying arterial pressure pulse waveform.

U.S. Pat. No. 5,584,298 to Kabal describes a noninvasive method for calculating stroke volume and cardiac output of a human heart using computerized algorithms. U.S. Pat. No. 5,758,652 to Nikolic describes a system and method for measuring the heart condition of a patient by utilizing blood pressure signals. U.S. Pat. No. 5,836,884 to Chio describes a method for determining the cardiovascular condition of a patient by determining peripheral resistance and diastolic flow velocity of the patient.

U.S. Pat. Nos. 5,390,679 and 5,797,395, both to Martin, relate to a cardiac output determining device and method which senses an arterial pressure waveform and compares the sensed waveform to a plurality of stored waveforms representative of known states. U.S. Pat. No. 5,913,826 to Blank describes an apparatus and method for assessing the cardiovascular status of a mammal by utilizing arterial pressure waveforms and systolic and diastolic pressures.

In summary, there are no simple and reliable indices of cardiac contractility, since they are not load independent. The most precise indices (dP/dt, Vmax, or Ees) require invasive and/or sophisticated techniques and usually no normal values have been defined. These indices have been more useful in assessing directional changes in cardiac contractility during acute interventions.

SUMMARY OF THE INVENTION

Cardiac contractility is the fundamental parameter of cardiac function, however its adequate assessment is precluded by methodological difficulties. The stroke volume (amount of blood ejected in each beat) is determined by three factors: cardiac contractility, preload, and afterload. Excluding cardiac contractility, the other three parameters may be properly quantified by known techniques. This invention provides methods and measurement systems for assessing the cardiac contractility of a cardiovascular system from the relationship of these other three, usually measurable variables.

One aspect of the present invention pertains to methods of determining the cardiac contractility of a cardiovascular system, which methods comprise the steps of (a) determining the stroke volume of the cardiovascular system; (b) determining the preload of the cardiovascular system; (c) determining the afterload of the cardiovascular system; and (d) utilizing the values of the stroke volume, the preload, and the afterload to calculate the cardiac contractility. In a preferred embodiment, the calculation of step (d) utilizes a mathematical relationship where the value of the preload, the value of the afterload, and the value of the cardiac contractility represent a length of one of the edges of each triangle in a tetrahedron, and the value of the stroke volume is represented by the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron. In one embodiment, the value of the preload comprises a parameter selected from the group consisting of end-diastolic volume, end-diastolic volume index, end-diastolic pressure, pulmonary capillary pressure, and end-diastolic stress. In one embodiment, the value of the afterload comprises a parameter selected from the group consisting of arterial pressure, arterial impedance, vascular resistance, and systolic stress.

Another aspect of the present invention pertains to methods of determining the cardiac contractility of a cardiovascular system, which methods comprise the step of utilizing the values representing the stroke volume, the preload, and the afterload of the cardiovascular system to calculate the cardiac contractility. In a preferred embodiment, the calculation utilizes a mathematical relationship where the value of the preload, the value of the afterload, and the value of the cardiac contractility represent a length of one of the edges of each triangle in a tetrahedron, and the value of the stroke volume is represented by the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron.

Another aspect of the present invention pertains to a measurement system for determining the cardiac contractility of a cardiovascular system, comprising (a) a system which determines the stroke volume of the cardiovascular system and which provides a signal representative of the stroke volume; (b) a system which determines the preload of the cardiovascular system and which provides a signal representative of the preload; (c) a system which determines the afterload of the cardiovascular system and which provides a signal representative of the afterload; and (d) a processor which (i) receives the signal representing the stroke volume; (ii) receives the signal representing the preload; (iii) receives the signal representing the afterload; and (iv) calculates the cardiac contractility from the signal representing the stroke volume, the signal representing the preload, and the signal representing the afterload. In a preferred embodiment, the mathematical relationship utilized to calculate the cardiac contractility comprises the preload, the afterload, and the cardiac contractility representing a length of one of the edges of each triangle in a tetrahedron, and the stroke volume representing the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron. In one embodiment, the signal representing the preload comprises a parameter selected from the group consisting of end-diastolic volume, end-diastolic volume index, end-diastolic pressure, pulmonary capillary pressure, and end-diastolic stress. In one embodiment, the signal representing the afterload comprises a parameter selected from the group consisting of arterial pressure, arterial impedance, vascular resistance, and systolic stress.

Still another aspect of this invention pertains to a measurement system for determining the cardiac contractility of a cardiovascular system, comprising a processor which (a) receives an input value representing the stroke volume of the cardiovascular system; (b) receives an input value representing the preload of the cardiovascular system; (c) receives an input value representing the afterload of the cardiovascular system; and (d) utilizes the input values representing the stroke volume, the preload, and the afterload to calculate the cardiac contractility. In a preferred embodiment, the mathematical relationship utilized to calculate the cardiac contractility comprises the input value representing preload, the input value representing afterload, and the cardiac contractility representing a length of one of the edges of each triangle in a tetrahedron, and the input value representing the stroke volume representing the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron.

DETAILED DESCRIPTION OF THE INVENTION

The performance of the left ventricle as a pump depends on the contraction of the sarcomeres in the myocardium as well as the loading conditions. The factors controlling myocardial function or shortening are myocardial contractility, afterload, and preload, as, for example, described in Am. J. Physiol., Vol. 202, pages 931 to 939 (1962) by Sonnenblick; Prog Cardiovasc. Dis., Vol. 16, pages 337 to 361 (1973) by Brutsacrt et al.; and Mechanics of Contraction of the Normal and Failing Heart, Braunweld (ed.), Little, Brown and Company, Boston, 1976, pages 39 to 71, by Braunwald et al. Preload is proportional to the stretch of the myocardium prior to stimulation and reflects the initial sarcomera length, and afterload is the load that the myocardium must bear to contract, as, for example, described in Mechanics of Contraction of the Normal and Failing Heart, Braunwald (ed.), Little, Brown and Company, Boston, 1976, pages 39 to 71, by Braunwald et al. Cardiac contractility reflects the level of activation and the formation and cycling of the cross bridges between actin and myosin filaments, as, for example, described in Heart Disease, Braunwald (ed.), W. B. Saunders Company, Philadelphia, 1997, pages 421 to 444, by Little et al.

For the heart as a chamber, myocardial shortening is expressed as the amount of blood ejected or stroke volume. In these conditions, preload is properly reflected by the end-diastolic volume, as, for example, described in Circ. Res., Vol. 35, pages 517 to 526 (1974) by Sonnenblick et al.; and Circ. Res., Vol. 21, pages 423 to 431 (1967) by Sonnenblick et al. Afterload can be represented as aortic impedance, as, for example, described in Circ. Res., Vol. 14, pages 283 to 293 (1964) by Wilcken et al.; Circ. Res., Vol. 40, page 451 (1977) by Nichols et al.; and J. Hypertension, Vol. 10, page 53 (1992) by O'Rourke et al. Afterload can also be represented as systemic vascular resistance, as, for example, described in Circ. Res., Vol. 9, pages 1148 to 1155 (1961) by Imperial et al.; and in "Clinical Measurement of Vascular Resistance and Assessment of Vasodilator Drugs" in Cardiac Catheterization, Angiography and Intervention, Grossman and Baim (ed.), Lea and Febiger, Philadelphia, 1991, page 143, by Grossman. In chronic conditions with alterations in the configuration of the left ventricle, afterload is adequately expressed as systolic stress, as, for example, described in Biophys. J., Vol. 9, pages 189 to 208 (1969) by Mirsky; Am. J. Cardiol., Vol. 34, pages 627 to 634 (1974) by Gould et al.; Circ. Res., Vol. 49, pages 829 to 842 (1981) by Yin; and Am. J. Physiol., Vol. 264, pages H1411 to H1421 (1993) by Regen et al. In the normal heart, the systolic blood pressure can be used as an afterload index since it determines the end-systolic volume, as, for example, described in Circ. Res., Vol. 35, pages 117 to 126 (1974) by Suga et al.;

*Circ. Res.,* Vol. 43, pages 677 to 687 (1978) by Sugawa; and *Circulation,* Vol. 69, pages 1058 to 1064 (1984) by Carabello et al. Only cardiac contractility remains as an elusive variable, with remarkable difficulties in its quantification as previously discussed herein.

Heart rate is the other fundamental variable of cardiac function, but its final effect on the stroke volume is mediated by alterations in loads, as, for example, described in *Br. Heart J.,* Vol. 57, pages 154 to 160 (1987) by Pierard et al. Its final effect on the stroke volume is also mediated by alterations in contractility (force-frequency relation), as, for example, described in *Arb. Physiol. Inst. Lpz.,* Vol. 6, page 139 (1871) by Bowditch; *Circulation,* Vol. 88, pages 2700 to 2704 (1993) by Mulleri et al.; *Circulation,* Vol. 88, pages 2962 to 2971 (1973) by Cooper; and *Circ. Res.,* Vol. 75, pages 434 to 442 (1994) by Hasenfuss et al. Heart rate behaves as a partial independent variable, as, for example, described in *Circulation,* Vol. 32, pages 549 to 558 (1965) by Ross et al.; and *Circulation,* Vol. 33, pages 933 to 944 (1966) by Benchimol et al. Heart rate has a clear impact on cardiac output (heart rate multiplied by stroke volume) only at very low or high frequency, as, for example, described in *Circ. Res.,* Vol. 8, pages 1254 to 1263 (1960) by Braunwald et al.

In the present invention, it is recognized that stroke volume is determined by cardiac contractility, preload, and afterload. Excluding cardiac contractility, all the other variables are well quantified by standard techniques. In this invention, we disclose a method and a system by which it is possible to quantify cardiac contractility from its relationship with these other, usually known variables. This is attained by the concept of stroke volume as a solid figure, with a tetrahedron shape and a volume equal to the value of this variable. Preload, afterload, and cardiac contractibility may be represented by a variety of lengths or heights of the sides, triangles, or tetrahedral form of the tetrahedron. Choice of these representations may be made by trying various representations on actual cardiac experimental data and assessing the reliability for measuring the cardiac contractibility. For example, in a preferred embodiment, the three edges that comprise each face of the tetrahedron were assigned to preload, afterload, and cardiac contractility. Knowing the amount of the stroke volume (volume of the figure), and the value of the preload and afterload (as the length of the first and second edge, respectively), the method of this invention calculates the length of the third edge (amount of cardiac contractility) that fits with the volume of the figure. Also, for example, in a most preferred embodiment, the calculation of cardiac contractility utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron.

The present invention comprises a simple and reliable method by which it is possible to assess cardiac contractility from its relationship to stroke volume, preload, and afterload. It comprises the concept of stroke volume as a three dimensional figure with a tetrahedron shape. As described above, in a preferred embodiment, the three edges that comprise the faces of the figure are assigned to preload, afterload, and cardiac contractility. Knowing the amount of stroke volume (volume of the figure) and the values of preload and afterload (as the length of the first and second edge, respectively), the method determines the length of the third edge (or amount of cardiac contractility) that fits with the volume of the figure.

For the construction and calibration of the method of the present invention, the normal values are obtained in basal conditions using any of the standard techniques suitable to measure stroke volume, preload (for example, end-diastolic volume), and afterload (for example, aortic impedance, systemic vascular resistance, systolic stress or systolic blood pressure). The amount of stroke volume is equal to the capacity of the tetrahedron. For preload and afterload, the control values are the normal values with a control value of 100 (units) being assigned to cardiac contractility (with a standard deviation given by the standard deviation of the other variables).

Utilizing this method to evaluate the cardiac contractility in a given patient only requires, for example, the actual values of stroke volume, any of the indices of preload such as end-diastolic volume, and any of the indices of afterload, and the method provides the amount of cardiac contractility, as, for example, described in Example 1.

As described above, in a most preferred embodiment, the value of the preload is represented by the length of the base of the base triangle of the tetrahedron, the value of the afterload is represented by the height of the base triangle of the tetrahedron, the value of the cardiac contractility is represented by the height of the tetrahedron, and the value of the stroke volume is represented by the volume of the tetrahedron. In order to calculate the value of the cardiac contractility from the value of the other three parameters, the analytical geometry for the volume of the tetrahedron may be used to derive the equation. The volume of the tetrahedron is known to be:

$$V = \frac{\text{Area of Base Triangle} * \text{Height of Tetrahedron}}{3}$$

where V is the volume of the tetrahedron and the symbol, *, as used herein, pertains to multiplication. In the methods of this invention, V represents the stroke volume (SV), and the height of the tetrahedron represents the value of cardiac contractility (C). The area of the base triangle of the tetrahedron is given by, $$\text{Area of Base Triangle} = \frac{\text{Length of Base} * \text{Height of Base Triangle}}{2}$$

Representing the length of base by preload (PRE) and the height of base triangle by afterload (AFTER), the equation converts to, $$\text{Area of Base Triangle} = \frac{\text{PRE} * \text{AFTER}}{2}$$

Substituting SV for V and C for the height of the tetrahedron and inserting the converted equation for the area of the base triangle, the equation becomes, $$SV = \frac{\text{PRE} * \text{AFTER} * C}{6}$$

Solving for C, the equation then becomes, $$C = \frac{SV * 6}{PRE * AFTER}$$

Thus, one aspect of the present invention pertains to methods of determining the cardiac contractility of a cardiovascular system, which methods comprise the steps of (a) determining the stroke volume of the cardiovascular system; (b) determining the preload of the cardiovascular system; (c) determining the afterload of the cardiovascular system; and (d) utilizing the values of the stroke volume, the preload, and the afterload to calculate the cardiac contractility. In a preferred embodiment, the calculation of step (d) utilizes a mathematical relationship where the value of the preload, the value of the afterload, and the value of the cardiac contractility represent a length of one of the edges of each triangle in a tetrahedron, and the value of the stroke volume is represented by the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron. In one embodiment, the value of the preload comprises a parameter selected from the group consisting of end-diastolic volume, end-diastolic volume index, end-diastolic pressure, pulmonary capillary pressure, and end-diastolic stress. In one embodiment, the value of the afterload comprises a parameter selected from the group consisting of arterial pressure, arterial impedance, vascular resistance, systolic pressure, and systolic stress.

Another aspect of the present invention pertains to methods of determining the cardiac contractility of a cardiovascular system, which methods comprise the step of utilizing the values representing the stroke volume, the preload, and the afterload of the cardiovascular system to calculate the cardiac contractility. In a preferred embodiment, the calculation utilizes a mathematical relationship where the value of the preload, the value of the afterload, and the value of the cardiac contractility represent a length of one of the edges of each triangle in a tetrahedron, and the value of the stroke volume is represented by the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron.

The methods of this invention disclosed herein provide the clinician with reliable and simple methods to assess cardiac contractility in order to increase the accuracy of the cardiac evaluation and improve the therapeutic management of the cardiovascular disorders. These novel methods allow a simple and reliable evaluation of cardiac contractility based in a comprehensive relationship of the fundamental parameters of ventricular function. Quantification of cardiac contractility by these methods is scarcely modified by loads, allowing a proper identification of inotropic abnormalities. These methods determine the amount of cardiac contractility responsible for an abnormal quantity of stroke volume, therefore providing useful information for diagnostic and therapeutic purposes. Additionally, to supply information about the inotropic state of the heart, these methods only need the input of well known hemodynamic variables, that may be obtained by any of the routinely used invasive or non-invasive techniques, as known in the art of cardiovascular measurements.

Considering that cardiovascular diseases are a leading cause of death, there is a strong need for a proper quantification of cardiac contractility. The methods of the present invention can be incorporated with all equipment and systems known in the art to evaluate ventricular function non-invasively such as echocardiography, radionuclide techniques or nuclear magnetic resonance, as well as in invasive techniques in the catheter lab, intensive care units or in surgery theatres, in order to provide a measurement system for determining the cardiac contractility of a cardiovascular system. These known systems for determining the stroke volume, the preload, the afterload, and other cardiovascular performance features may include or be combined with a suitable processor, such as a computer capable of processing digital signals or even manual calculation using the mathematical relationship of the methods of this invention to provide a measurement system to determine cardiac contractility. The measurement system of this invention may further comprise a display device which receives the value of cardiac contractility from the processor and displays that value, such as a display device comprising a monitor that visually displays the cardiac contractility. Also, the display device may be a recorder that records the cardiac contractility. The measurement system of this invention may operate in real time and may provide a continuous determination of the cardiac contractility of the patient or, alternatively, may operate in a time delay from real time operation.

Thus, one aspect of the present invention pertains to a measurement system for determining the cardiac contractility of a cardiovascular system, comprising (a) a system which determines the stroke volume of the cardiovascular system and which provides a signal representative of the stroke volume; (b) a system which determines the preload of the cardiovascular system and which provides a signal representative of the preload; (c) a system which determines the afterload of the cardiovascular system and which provides a signal representative of the afterload; and (d) a processor which (i) receives the signal representing the stroke volume; (ii) receives the signal representing the preload; (iii) receives the signal representing the afterload; and (iv) calculates the cardiac contractility from the signal representing the stroke volume, the signal representing the preload, and he signal representing the afterload. In a preferred embodiment, the mathematical relationship utilized to calculate the cardiac contractility comprises the preload, the afterload, and the cardiac contractility representing a length of one of the edges of each triangle in a tetrahedron, and the stroke volume representing the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron. In one embodiment, the signal representing the preload comprises a parameter selected from the group consisting of end-diastolic volume, end-diastolic volume index, end-diastolic pressure, pulmonary capillary pressure, and end-diastolic stress. In one embodiment, the signal representing the afterload comprises a parameter selected from the group consisting of arterial pressure, arterial impedance, vascular resistance, and systolic stress.

Still another aspect of this invention pertains to a measurement system for determining the cardiac contractility of a cardiovascular system, comprising a processor which (a) receives an input value representing the stroke volume of the cardiovascular system; (b) receives an input value representing the preload of the cardiovascular system; (c) receives an input value representing the afterload of the cardiovascular system; and (d) utilizes the input values representing the stroke volume, the preload, and the afterload to calculate the cardiac contractility. In a preferred embodiment, the mathematical relationship utilized to calculate the cardiac contractility comprises the input value representing preload, the input value representing afterload, and the cardiac contractility representing a length of one of the edges of each triangle in a tetrahedron, and the input value representing the stroke volume representing the volume of the tetrahedron. In a most preferred embodiment, the calculation of step (d) utilizes a mathematical relationship where the value of the stroke volume is represented by the volume of a tetrahedron, the value of the preload is represented by a length of the base of the base triangle of the tetrahedron, the value of the afterload is represented by the height of the base triangle of the tetrahedron, and the value of the cardiac contractility is represented by the height of the tetrahedron.

EXAMPLES

Several embodiments of the present invention are described in the following examples, which are offered by way of description and not by way of limitation.

The capability of the method of the present invention to assess cardiac contractility was evaluated using data from several experiments published in the literature and suitable for analysis. In this approach, afterload in the method was expressed as systolic pressure. Since different methodologies to measure cardiac contractility were used, the comparison between them was attained by analyzing the amount of changes (delta values) and were statistically treated using paired t test, ANOVA, correlation, and agreement between methods when applicable, as, for example, described in *Lancet*, Vol. 1, pages 307 to 310 (1986) by Bland et al.

Example 1

Hemodynamic data was utilized from Takeuchi et al. ("Single-Beat Estimation of the Slope of the End-Systolic Pressure-Volume Relation in the Human Left Ventricle". *Circulation*, Vol. 83, pages 202 to 212 (1991)).

|  | Preload | Afterload | Stroke Volume |
|---|---|---|---|
|  | Pre_adj | After_adj | SV_adj |
| Control state Mean value | 70 | 109 | 40 |

| Cases Receiving Angiotensin | | | |
|---|---|---|---|
| Case Number | Pre_v | After_v | SV_v |
| 1 | 68 | 142 | 41 |
| 2 | 119 | 155 | 38 |
| 3 | 66 | 176 | 30 |
| 4 | 78 | 164 | 34 |

-continued

| Cases Receiving Angiotensin | | | |
|---|---|---|---|
| Case Number | Pre_v | After_v | SV_v |
| 5 | 79 | 156 | 40 |
| 6 | 82 | 142 | 50 |
| 7 | 95 | 145 | 36 |
| 8 | 93 | 125 | 60 |

Initially, to calibrate the model of the method of this invention, the average mal (or control state) values were used:

Preload (end-diastolic volume) = 70 (Pre_adj)
Afterload (Systolic pressure) = 109 (After_adj)
Stroke volume (SV) = 40 (SV_adj)
Cardiac contractility (C) = 100 (C_adj)

Thereafter, the C value in each case during angiotension infusion was calculated using its corresponding value of preload, afterload and stroke volume. For instance, for the first case receiving angiotenison, where:

Pre_v=68
After_v=142
SV_v=41

The first step was to obtain the edge value for the tetrahedron for the control state using the standard mathematical equation for the volume of a tetrahedron:

$$Edge = \sqrt[3]{6 * sv\_adj}$$

Therefore, for the control state, $$Edge = \sqrt[3]{6 * 40} = 6.214465$$

The next step was to obtain the unitary (u) values of preload (pre_u) and afterload (after_u).

$$Pre\_u = pre\_v * (edge / pre\_adj)$$

$$After\_u = (after\_v - after\_adj) * \frac{(-1) * edge}{500 - after\_adj} + edge$$

where, for example, in Case 1 and in the control state,

Pre_v=68
After_v=142
Pre_adj=70
After_adj=109

Therefore, substituting these values, $$Pre\_u = 68 * (6.214465/70) = 6.036908$$

$$After\_u = (142 - 109) * \frac{(-1) * 6.214465}{500 - 109} + 6.214465 = 5.68997$$

In order to obtain the unitary (u) value of C, using the equation derived herein for cardiac contractibility, $$C\_u = \frac{SV * 6}{Pre\_u * after\_u} = \frac{41 * 6}{6.036908 * 5.68997} = 7.161608$$

Therefore, the value of C (C_v) for Case 1 is:

$$C\_v = \frac{C\_u}{edge} * 100 = \frac{7.161608}{6.214465} * 100 = 115.2409$$

Thus, during angiotensin treatment, the corresponding C values for Cases 1 to 8 were calculated using the method of this invention to be as follows:

| Case | C |
|---|---|
| 1 | 115.24 |
| 2 | 63.33 |
| 3 | 95.99 |
| 4 | 88.76 |
| 5 | 100.71 |
| 6 | 116.54 |
| 7 | 73.04 |
| 8 | 117.72 |

The steps described above can be represented by the following computer processing flow chart:

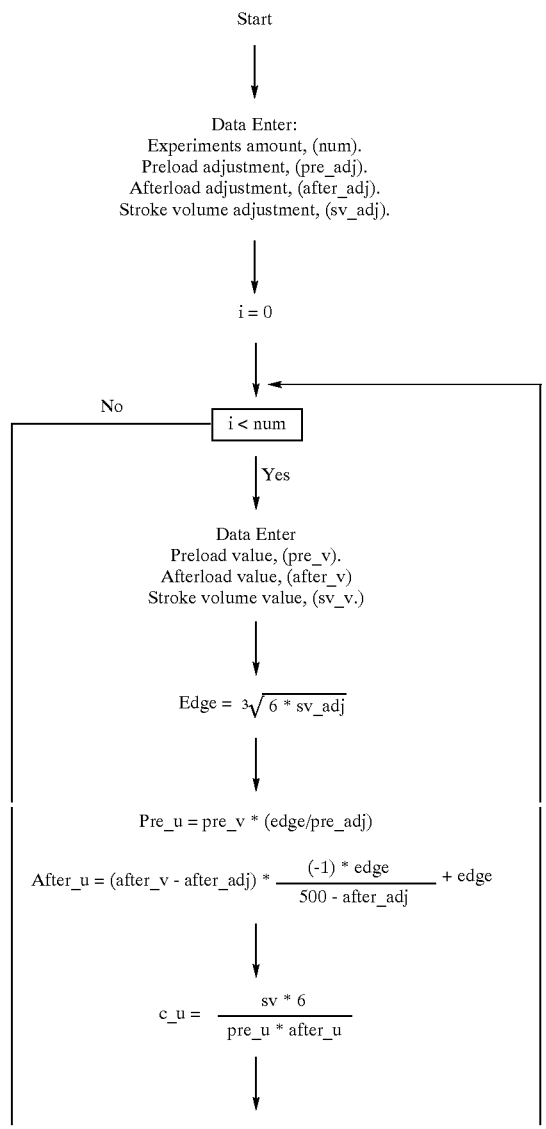

Example 2

Cardiovascular data was utilized from "Left Ventricular Pressure/Volume Relationship in Coronary Artery Disease," *Am. Heart J.,* Vol. 112, pages 375 to 381 (1981) by Isakadrian et al. This study was done in normal subjects and in patients with different degrees of coronary artery disease with the normal ejection fraction evaluated by radionuclide techniques. The changes in cardiac contractility induced by aerobic exercise were assessed by ejection fraction and ESP/ESV (end-systolic pressure/end-systolic volume) relationship. The method of the present invention, as described herein, was utilized to calculate the changes in cardiac contractility. The results were comparable in the four groups studied, and a good correlation was found between the two standard methods and the method of the present invention ( r values higher than 0.96).

Example 3

Cardiovascular data was utilized from "Single-beat Estimation of the Slope of the End-Systolic Pressure-Volume Relation in the Human Left Ventricle," *Circulation,* Vol. 83, pages 202 to 212 (1991) by Takeuchi et al. This study involved 25 patients, most of them with coronary artery disease. 7 of these patients had an ejection fraction lower than 50%. Hemodynamic modifications were measured with high-fidelity micromanometer and ventriculography. Alterations in cardiac contractility induced by modifications in loads using angiotensin or nitroglycerin tended to be lower when they were measured with the method of this invention (0.4% and −4%, respectively) in comparison to the measurements made with ejection fraction (−10.3% and 8.3%) or ESP/ESV (9.1% and 9%). The increase in cardiac contractility using dobutamine induced changes measured y the method of this invention was 23% in comparison to the measurements made with ejection fraction of 15% and with ESP/ESV of 32%.

Example 4

Cardiovascular data was utilized from "Sensitivity of End-Systolic Pressure-Dimension and Pressure-Volume Relations to the Inotropic State in Humans," *Circulation,* Vol. 65, pages 988 to 997 (1982) by Borow et al. Ten normal subjects were studied echocardiographically. With the increase in blood pressure induced with methoxamine, cardiac contractility assessed with the method of this invention changed 1.4%, and with ejection fraction measurement, it changed −10.4% ( p less than 0.05). The increase in cardiac contractility with the use of dobutamine was higher when measured with ESP/ESV (57.6%) than when measured with ejection fraction (12.8%) or with the use of the method of this invention (27.5%).

Example 5

Cardiovascular data was utilized from "Left Ventricular Function in Coronary Artery Disease," *J. Am. Coll. Cardiol.*, Vol. 3, pages 781 to 788 (1984) by El-Tobgi et al. In this study, normal subjects (group I) were compared with two groups of patients with coronary artery disease (groups II and III, the last one with ventricular dysfunction) and studied with tip-manometer catheter and ventriculography measurements. In basal conditions, the method of this invention behaves similar to the ejection fraction in detecting depression in cardiac contractility in group III (−17.2% and −18.0%, respectively). However in group I, with the increase in blood pressure attained with phenylephrine, ejection fraction did not show a significant change (−0.1%) while the method of the present invention showed an increase of 10.4% as expected in the presence of a drop in heart rate induced by an alpha-I adrenoceptor stimulation, as, for example, described in *J. Cardiovasc. Pharmacol.*, Vol. 14, pages 603 to 609 (1989) by Curiel et al. In group III, with the increase in blood pressure, there was a fall in all the indices, although the fall was much lower with the use of the method of this invention (−15.8%), than when measured with ejection fraction (−25.3%) or ESP/ESV (−51.9%).

Example 6

Cardiovascular data was utilized from "The Linearity of the End-Systolic Pressure-Volume Relationship in Man and its Sensitivity for Assessment of Left Ventricular Function," *Circulation*, Vol. 63, pages 1216 to 1222 (1981) by Mehmel et al. This study was performed in patients with coronary artery disease and with catheter-tip manometer and ventricular angiogram measurements. Load modifications induced by methoxamine and nitrates produced small changes in cardiac contractility when assessed utilizing the method of this invention (3.3% and −1.7%, respectively). These values were statistically different to the changes measured using ejection fraction (−5.0% and 5.0%, respectively).

Example 7

Cardiovascular data was utilized from "Alterations in Preload and Ejection Phase Indices of Left Ventricular Performance," *Circulation*, Vol. 51, pages 910 to 915 (1975) by Rankin et al. In this study, during tilt test, ten normal volunteers were evaluated echocardiographically, and changes in cardiac contractility were measured with ejection fraction (−6.9%) and using velocity of shortening (2.8%). Application of the method of this invention gave a value for changes in cardiac contractility of −6.9%. The correlation coefficient (r) between these variables was higher than 0.96.

Example 8

Cardiovascular data was utilized from "Left Ventricular Function and Hyperthyroidism," *Br. Heart J.*, Vol. 46, pages 137 to 143 (1981) by Merillon et al. In patients with hyperthyroidism and invasive assessment of ventricular function, the administration of propranolol produced a fall in cardiac contractility. This change was similar when the inotropic state was assessed by means of P/V ratio (−28%), ejection fraction (−19%), dP/dt (−20%), and dP/dt/TP (−19%). Use of the method of the present invention gave a value for the change in cardiac contractility of −17%. Use of the velocity of shortening and ESP/ESV both showed a different value (−32%).

Example 9

Cardiovascular data was utilized from "Comparative Efficacy of Three Indices of Left Ventricular Performance Derived from Pressure-Volume Loops in Heart Failure Induced by Tachypacing,"*J. Am. Coll. Cardiol.*, Vol. 23, pages 209 to 218 (1984) by Rahko. In this study, dogs chronically instrumented with progressive heart failure induced by tachypacing, showed a progressive drop (weeks 1, 2, and 3) in cardiac contractility when assessed with the method of this invention (−28.8%, −50.6%, and −54.7%, respectively). These amounts were comparable to the fall in cardiac contractility measured by ejection fraction or by ESP/ESV. Changes in dP/dt were clearly lower (−18.6%, −30.1%, and −39.1%, respectively).

Example 10

Cardiovascular data was utilized from "Effect of Regional Ischemia on Left Ventricular End-Systolic Pressure-Volume Relation in Chronically Instrumented Dogs,"*J. Am. Coll. Cardiol.*, Vol. 5, pages 297 to 302 (1985) by Little et al. In this study, the effect of a segmental depression of left ventricular contraction, produced by occlusion of a coronary artery, was evaluated by ejection fraction (−19.5%) and ESP/ESV (−2.9%). Applying the method of the present invention, the drop in the inotropic state was higher (−23.0%).

Example 11

Cardiovascular data was utilized from "Mechanism of Global Functional Recovery Despite Sustained Postischemic Regional Stunning," *Circulation*, Vol. 85, pages 816 to 827 (1992) by Lawrence et al. These experiments were carried out in open-chest reflex-blocked dogs. During ischemia induced by coronary occlusion, there was a fall in cardiac contractility expressed as changes in ejection fraction (−15.7%), ESP/ESV (−11.6%), and dP/dt (−8.6%). When the method of this invention was utilized, the fall in cardiac contractility was −16.7%.

Example 12

Cardiovascular data was utilized from "Response of the Left Ventricular End-Systolic Pressure-Volume Relation in Conscious Dogs to a Wide Range of Contractile States," *Circulation*, Vol. 78, pages 736 to 745 (1988) by Little et al. In this study, the contractile state was increased by dobutamine and decreased by verapamil. The method of this invention showed changes (11.7% and −23%, respectively) that were similar to these changes measured by ejection fraction (17.1% and −10.9%, respectively), but different than when measured by ESP/ESV (150% and −38.5%) and dP/dt (34.1% and −39.9%).

Example 13

Cardiovascular data was utilized from "Effects of Changes in Preload, Afterload and Inotropic State on Ejection and Isovolumic Phase Measures of Contractility in the Conscious Dog," *Am. J. Cardiol.*, Vol. 35, pages 623 to 634 (1975) by Mahler et al. In this study, increase in preload was attained by Ringer's solution infusion, and rise of blood pressure with phenylephrine administration. In these conditions, the method of the present invention remains notably constant (7.3% and 0.8%, respectively), and better than the methods of dP/dt (11% and −2%/), dP/dt DP40 (10% and 2%), and Vcf (−7% and −26%). The method of this invention was less sensitive than the other indices to measure changes in the inotropic state induced with isoproterenol or propranolol. Thus, the values obtained with the method of the present invention (20.3% and −4.8%, respectively) were lower than those obtained with dP/dt (55% and −18%), dP/dt DP40 (56% and −13%), and Vcf (53% and −18%).

The results on humans from Examples 2 to 8 from using the method of this invention in comparison to using ejection fraction or ESP/ESV are summarized in Table 1.

TABLE 1

| Example No. | Procedure Applied To Humans | Method of This Invention Avg. Value (SD) | EF Avg. Value (SD) | ESP/ESV Avg. Value (SD) |
|---|---|---|---|---|
| 2 | Control Healthy | 100.0 | 60 | 4.4 |
| 2 | Control 0V | 102.3 | 61 | 4.6 |
| 2 | Control 1V | 100.4 | 61 | 4.7 |
| 2 | Control MV | 101.3 | 60 | 4.3 |
| 2 | Exercise Healthy | 142.6 | 72 | 8.7 |
| 2 | Exercise 0V | 122.6 | 65 | 7.3 |
| 2 | Exercise 1V | 114.7 | 61 | 5.4 |
| 2 | Exercise MV | 107.1 | 57 | 4.6 |
| 3 | Control 1 | 99.8 (11.5) | 58 (7) | 4.4 (1.8) |
| 3 | Angiotensin | 100.2 (21.3) | 52 (11)[a] | 4.8 (1.8) |
| 3 | Control 2 | 101.2 (15.5) | 60 (8) | 5.6 (2.5) |
| 3 | Nitroglycerin | 97.1 (14.6) | 65 (8)[a] | 6.1 (3.1) |
| 4 | Control | 99.7 (4.6) | 60.0 (2.9) | |
| 4 | Methoxamine | 101.2 (6.3) | 53.8 (3.8)[a] | 3.1 (0.5) |
| 4 | Dobutamine | 127.2 (6.7)[a] | 67.7 (3.3)[a] | 4.8 (1.1)[a] |
| 5 | Control Healthy | 100.0 | 67.6 | |
| 5 | Control CAD | 99.5 | 65.8 | |
| 5 | Control CAD, VD | 82.8 | 55.4 | |
| 5 | Phenylephrine Healthy | 110.4 | 67.5 | 10.4 |
| 5 | Phenylephrine CAD | 107.3 | 64.0 | 9.9 |
| 5 | Phenylephrine CAD + VD | 84.2 | 50.5 | 5.0 |
| 6 | Control | 105.0 (21.2) | 60 (12) | |
| 6 | Nitrate | 103.2 (17.4) | 63 (11)[a] | |
| 6 | Methoxamine | 108.5 (29.8) | 57 (14)[a] | |
| 7 | Control | 99.9 (8.3) | 70.0 (4.8) | |
| 7 | Head-up Tilt | 93.0 (11.3) | 65.3 (6.9) | |
| 8 | Control | 113.7 (13.9) | 69.6 (6.8) | 2.2 (0.8) |
| 8 | Propranolol | 94.3 (13)[a] | 56.3 (7.4)[a] | 1.5 (0.5)[a] |

[a] $p$ less than 0.05

In Table 1, SD=standard deviation; CAD=coronary artery disease; EF=ejection fraction expressed in terms of percentage; ESP/ESV=end-systolic pressure/end-systolic volume relation expressed in units of mm Hg per ml; MV=multiple vassels; V=vassel; and VD=ventricular dysfunction. Examples 3, 4, 6, 7, and 8 with individual case parameters reported were analyzed using absolute values. Cardiac contractility assessed with the method of this invention was not significantly modified by changes in loads and properly identified inotropic interventions. The cardiac contractility index of ESP/ESV and the values from the method of this invention showed similar results while ejection fraction was significantly modified by loads. Examples 2 and 5 reported their findings as average values.

The results on animals from Examples 9 to 12 from using the method of this invention in comparison to using ejection fraction and ESP/ESV are summarized in Table 2.

TABLE 2

| Example No. | Procedure Applied to Animals | Method of This Invention Avg. Value | EF Avg. Value | ESP/ESV Avg. Value |
|---|---|---|---|---|
| 9 | Control | 100.0 | 37 | 6.3 |
| 9 | Pacing W1 | 71.2 | 26 | 4.5 |
| 9 | Pacing W2 | 49.4 | 21 | 3.6 |
| 9 | Pacing W3 | 45.3 | 16 | 2.8 |
| 10 | Control | 100.0 | 29 | 6.9 |
| 10 | Ischemia | 77.0 | 23.9 | 6.7 |
| 11 | Control | 100.0 | 38.1 | 4.3 |
| 11 | Ischemia | 83.3 | 32.1 | 3.8 |
| 12 | Control 1 | 100.0 | 46.8 | 7.4 |
| 12 | Dobutamine | 111.7 | 54.8 | 18.5 |
| 12 | Control 2 | 100.0 | 44.0 | 8.3 |
| 12 | Verapamil | 77.1 | 39.2 | 5.1 |

In Table 2, W = week; EF = ejection fraction expressed in terms of percentage; and ESP/ESV = end-systolic pressure/end-systolic volume relation expressed in units of mm Hg per ml. Examples 9 to 12 reported their findings as average values.

The results on animals from Example 13 from using the method of this invention in comparison to using velocity of shortening and dP/dT are summarized in Table 3.

TABLE 3

| Example No. | Procedure Applied to Animals | Method of This Invention Avg. Value | Vcf Avg. Value | dP/dT Avg. Value |
|---|---|---|---|---|
| 13 | Control 1 | 100.0 | 2.30 | 3890 |
| 13 | Volume | 107.3 | 2.11 | 4320 |
| 13 | Control 2 | 100.0 | 2.13 | 3810 |
| 13 | Phenylephrine | 100.8 | 1.61 | 3670 |
| 13 | Control 3 | 100.0 | 1.89 | 3530 |
| 13 | Isoproterenol | 120.3 | 2.83 | 5430 |
| 13 | Control 4 | 100.0 | 2.22 | 3660 |
| 13 | Propranolol | 95.2 | 1.80 | 3000 |

In Table 3, Vcf = velocity of shortening expressed in terms of circulation per second; and dP/dT is the change in pressure per time expressed in terms of mm Hg per second. Example 13 reported its findings as average values.

The performance of the method of the present invention using wall stress instead of systolic arterial pressure as the measure of afterload was evaluated, especially in dilated hearts. End-systolic meridional and/or circumferential stress were chosen for analysis since they were the type of stress most frequently used in studies of humans. In addition, conversion to a single unit (Kdynes/cm$^2$) was done. The isovolumetric stress was determined using the same methodology previously described for isovolumetric pressure. A value of 600 Kdynes/cm$^2$ for meridional stress and 1100 Kdynes/cm$^2$ for circumferential stress was obtained and used in all experiments. No significant differences in cardiac contractility values were observed using either systolic arterial pressure or ventricular wall stress, even in dilated hearts. Thus, in relation to systolic blood pressure, no statistical difference and excellent correlation of cardiac contractility values were observed in all instances with meridional stress and with circumferential stress.

It can be seen from the above examples that the method and system of the present invention was utilized in a variety of experimental conditions and proved to be useful in humans (Examples 1 to 8) and in animals (Examples 9 to 13), including normal subjects (Examples 2, 4, 5, and 7), patients with cardiac diseases (Examples 2, 3, 5, 6, and 8), basal conditions (Examples 2 and 5), and with interventions (Examples 3, 4, and 6 to 13). With alterations in loads, the method of this invention was less modified than the other indices (Examples 3 to 6 and 13). With manipulations of cardiac contracility, in some experiments, it was more sensitive (Examples 3 and 9 to 11), similar in many others (Examples 4, 7 to 9, and 12), and less sensitive in some of them (Examples 3, 4, 12, and 13), especially in animals. The method and system of the present invention is only minimally affected by these hemodynamic loads and has an adequate sensitivity to identify changes in cardiac contractility, making it a suitable tool to assess the inotropic state of the heart. Also, it measures the amount of cardiac contractility responsible for the abnormal quantity of stroke volume, therefore providing useful information for diagnostic and therapeutic purposes. The method and system of this invention may be incorporated into equipment and techniques known for non-invasive evaluations of ventricular function, such as echocardiography, radionuclide techniques, and nuclear magnetic resonance, as well as into invasive equipment and techniques, such as used in the catheter laboratory, intensive care units, and surgery areas.

While the invention has been described in detail and with reference to specific embodiments thereof, it will be apparent to one skilled in the art that various changes and modifications can be made without departing from the spirit and scope thereof.

What is claimed is:

1. A method of determining the cardiac contractility of a cardiovascular system, said method comprising the steps of:
    (a) determining the stroke volume of the cardiovascular system;
    (b) determining the preload of the cardiovascular system;
    (c) determining the afterload of the cardiovascular system; and
    (d) utilizing the values of said stroke volume, said preload, and said afterload to calculate said cardiac contractility.

2. The method of claim 1, wherein the calculation of step (d) utilizes a mathematical relationship where the value of said stroke volume is represented by the volume of a tetrahedron, the value of said preload is represented by a length of the base of the base triangle of said tetrahedron, the value of said afterload is represented by the height of the base triangle of said tetrahedron, and the value of said cardiac contractility is represented by the height of said tetrahedron.

3. The method of claim 1, wherein the calculation of step (d) utilizes a mathematical relationship where the value of said preload, the value of said afterload, and the value of said cardiac contractility represent a length of one of the edges of each triangle in a tetrahedron, and the value of said stroke volume is represented by the volume of said tetrahedron.

4. The method of claim 1, wherein the value of said preload comprises a parameter selected from the group consisting of end-diastolic volume, end-diastolic volume index, end-diastolic pressure, pulmonary capillary pressure, and end-diastolic stress.

5. The method of claim 1, wherein the value of said afterload comprises a parameter selected from the group consisting of arterial pressure, arterial impedance, vascular resistance, systolic pressure, and systolic stress.

6. The method of claim 1 wherein said preload includes end-diastolic volume and said afterload includes systolic pressure.

7. The method of claim 1 wherein a normal value of said cardiac contractility is normalized at a nominal value of 100.

8. The method of claim 7 wherein a cardiac contractility of greater than 100 represents a higher than normal cardiac contractility and a cardiac contractility less than 100 represents a lower than normal cardiac contractility.

9. A measurement system for determining the cardiac contractility of a cardiovascular system, comprising:
    (a) a system which determines the stroke volume of the cardiovascular system and which provides a signal representative of said stroke volume;
    (b) a system which determines the preload of the cardiovascular system and which provides a signal representative of said preload;
    (c) a system which determines the afterload of the cardiovascular system and which provides a signal representative of said afterload; and
    (d) a processor which:
        i. receives said signal representing said stroke volume;
        ii. receives said signal representing said preload;
        iii. receives said signal representing said afterload; and
        iv. calculates said cardiac contractility utilizing said signal representing said stroke volume, said signal representing said preload, and said signal representing said afterload.

10. The measuring system of claim 9, wherein the calculation of step (d) utilizes a mathematical relationship where the value of said stroke volume is represented by the volume of a tetrahedron, the value of said preload is represented by a length of the base of the base triangle of said tetrahedron, the value of said afterload is represented by the height of the base triangle of said tetrahedron, and the value of said cardiac contractility is represented by the height of said tetrahedron.

11. The measurement system of claim 9, wherein the mathematical relationship utilized to calculate said cardiac contractility comprises said preload, said afterload, and said cardiac contractility representing a length of one of the edges of each triangle in a tetrahedron, and said stroke volume representing the volume of said tetrahedron.

12. The method of claim 9, wherein said signal representing said preload comprises a parameter selected from the group consisting of end-diastolic volume, end-diastolic volume index, end-diastolic pressure, pulmonary capillary pressure, and end-diastolic stress.

13. The method of claim 9, wherein said signal representing said afterload comprises a parameter selected from the group consisting of arterial pressure, arterial impedance, vascular resistance, and systolic stress.

14. A measurement system for determining the cardiac contractility of a cardiovascular system, comprising a processor which:
    (a) receives an input value representing the stroke volume of the cardiovascular system;
    (b) receives an input value representing the preload of the cardiovascular system;
    (c) receives an input value representing the afterload of the cardiovascular system; and
    (d) calculates said cardiac contractility utilizing said input value representing said stroke volume, said input value representing said preload, and said input value representing said afterload.

15. The measurement system of claim 14, wherein the calculation of step (d) utilizes a mathematical relationship where the value of said stroke volume is represented by the volume of a tetrahedron, the value of said preload is represented by a length of the base of the base triangle of said tetrahedron, the value of said afterload is represented by the height of the base triangle of said tetrahedron, and the value of said cardiac contractility is represented by the height of said tetrahedron.

16. The measurement system of claim 14, wherein the mathematical relationship utilized to calculate said cardiac contractility comprises said input value representing said preload, said input value representing said afterload, and said cardiac contractility representing a length of one of the edges of each triangle in a tetrahedron, and said input value of said stroke volume representing the volume of said tetrahedron.

17. A method of determining the cardiac contractility of a cardiovascular system, said method comprising the step of utilizing values representing the stroke volume, the preload, and the afterload of said cardiovascular system to calculate said cardiac contractility.

18. The method of claim 17, wherein the calculation of said cardiac contractility utilizes a mathematical relationship where the value of said stroke volume is represented by the volume of a tetrahedron, the value of said preload is represented by a length of the base of the base triangle of said tetrahedron, the value of said afterload is represented by the height of the base triangle of said tetrahedron, and the value of said cardiac contractility is represented by the height of said tetrahedron.

19. The method of claim 17, wherein the calculation of said cardiac contractility utilizes a mathematical relationship where the value of said preload, the value of said afterload, and the value of said cardiac contractility represent a length of one of the edges of each triangle in a tetrahedron, and the value of said stroke volume is represented by the volume of said tetrahedron.

* * * * *

UNITED STATES PATENT AND TRADEMARK OFFICE
CERTIFICATE OF CORRECTION

PATENT NO.    : 6,440,078 B1                                        Page 1 of 1
DATED         : August 27, 2002
INVENTOR(S)   : Roberto Curiel et al.

It is certified that error appears in the above-identified patent and that said Letters Patent is hereby corrected as shown below:

<u>Title page,</u>
Item [75], Inventor, "Ruben Landecta" surname should be changed to -- Landaeta --

Signed and Sealed this

Eleventh Day of March, 2003

JAMES E. ROGAN
*Director of the United States Patent and Trademark Office*